United States Patent
Stokman et al.

(10) Patent No.: US 11,961,330 B2
(45) Date of Patent: Apr. 16, 2024

(54) SYSTEM TO NOTIFY A REQUEST FOR HELP BY DETECTING AN INTENT TO PRESS A BUTTON, SAID SYSTEM USING ARTIFICIAL INTELLIGENCE

(71) Applicant: Kepler Vision Technologies B.V., Amsterdam (NL)

(72) Inventors: Henricus Meinardus Gerardus Stokman, Amsterdam (NL); Marc Jean Baptist van Oldenborgh, Amsterdam (NL)

(73) Assignee: Kepler Vision Technologies B.V., Amsterdam (NL)

( * ) Notice: Subject to any disclaimer, the term of this patent is extended or adjusted under 35 U.S.C. 154(b) by 676 days.

(21) Appl. No.: 17/069,207

(22) Filed: Oct. 13, 2020

(65) Prior Publication Data
US 2021/0110922 A1    Apr. 15, 2021

(30) Foreign Application Priority Data

Oct. 11, 2019 (EP) .................................. 19202867

(51) Int. Cl.
*G06V 40/20* (2022.01)
*G06N 20/00* (2019.01)
(Continued)

(52) U.S. Cl.
CPC ............. *G06V 40/20* (2022.01); *G06N 20/00* (2019.01); *G06V 10/764* (2022.01); *G06V 10/82* (2022.01); *G06V 20/52* (2022.01); *G16H 40/63* (2018.01)

(58) Field of Classification Search
CPC ...... G06V 40/20; G06V 10/764; G06V 10/82; G06V 20/52; G06N 20/00; G16H 40/63; G06F 18/24143
See application file for complete search history.

(56) References Cited

U.S. PATENT DOCUMENTS 10,370,191 B2    8/2019  Galewyrick et al.
10,406,045 B2    9/2019  Hayes et al.
(Continued)

FOREIGN PATENT DOCUMENTS

WO     02075687 A2    9/2002
WO    2019193409 A1   10/2019

OTHER PUBLICATIONS

El Kaid Amal et al: "Reduce False Positive Alerts for Elderly Person Fall Video-Detection Algorithm by Convolutional Neural Network Model" Procedia Computer Science, vol. 148, Feb. 23, 2019, pp. 2-11, XP085609231, ISSN: 1877-0509, DOI: 10.1016/J.PROCS.2019.01.004.
(Continued)

*Primary Examiner* — Lewis G West
(74) *Attorney, Agent, or Firm* — AEON Law, PLLC; Adam L. K. Philipp; David Cohen

(57) ABSTRACT

There is provided a system configured to trigger system configured to trigger a function, said system comprising:
at least one actuator that is associated with said function;
an image capturing sensor;
a computing device comprising a data processor, and
a computer program product comprising a machine learning model trained for detecting an intent of a person to operate said at least one actuator,
wherein said computer program product when running on said data processor:
receives at least one image from said image capturing sensor;
analyzes said at least one image, the analyzing comprises:
subjecting said at least one image to said machine learning model;
detecting presence of said intent to operate said at least one actuator in said at least one image, and
(Continued)

triggers said function upon detecting said intent.

4 Claims, 6 Drawing Sheets

(51) Int. Cl.
  *G06V 10/764* (2022.01)
  *G06V 10/82* (2022.01)
  *G06V 20/52* (2022.01)
  *G16H 40/63* (2018.01)

(56) References Cited

U.S. PATENT DOCUMENTS

| | | | |
|---|---|---|---|
| 11,126,283 B2* | 9/2021 | Chen | G06F 3/0416 |
| 2012/0169872 A1* | 7/2012 | Williamson | G08B 13/19615 |
| | | | 348/143 |
| 2012/0282974 A1* | 11/2012 | Green | G08B 13/19684 |
| | | | 455/550.1 |
| 2014/0266669 A1* | 9/2014 | Fadell | G05B 19/042 |
| | | | 340/501 |
| 2015/0193142 A1* | 7/2015 | Min | G06F 3/016 |
| | | | 715/773 |
| 2017/0357521 A1* | 12/2017 | Paek | G06F 3/0488 |
| 2018/0005024 A1* | 1/2018 | Leppänen | G06V 40/20 |
| 2018/0314897 A1 | 11/2018 | Camilus et al. | |
| 2019/0206218 A1 | 7/2019 | Kusens et al. | |
| 2019/0294871 A1 | 9/2019 | Joze et al. | |
| 2019/0300002 A1 | 10/2019 | Fung et al. | |
| 2019/0306664 A1 | 10/2019 | Mehta et al. | |
| 2020/0409469 A1* | 12/2020 | Kannan | G06Q 50/20 |
| 2021/0026464 A1* | 1/2021 | Yamada | G06F 3/0346 |
| 2021/0103348 A1* | 4/2021 | Jeppsson | G06F 3/04845 |
| 2021/0124422 A1* | 4/2021 | Forsland | G06F 1/1694 |
| 2021/0362602 A1* | 11/2021 | Anti | G06F 3/044 |
| 2022/0067131 A1* | 3/2022 | Lock | G06F 21/32 |
| 2022/0094782 A1* | 3/2022 | Mendiratta | G06F 18/22 |
| 2022/0203996 A1* | 6/2022 | Katz | B60W 50/14 |
| 2023/0071994 A1* | 3/2023 | Day | A61B 5/7275 |
| 2023/0076068 A1* | 3/2023 | Li | G06F 3/017 |
| 2023/0222737 A1* | 7/2023 | Yalawarmath | G06Q 10/10 |
| | | | 345/419 |

OTHER PUBLICATIONS

Z.Z.Bien et al: "Intention Reading is Essential in Human-Friendly Interfaces for the Elderly and the Handicapped", IEEE Transactions on Industrial Electronics., vol. 52, No. 6, Dec. 1, 2005, pp. 1500-1501, XP055679505, USA ISSN: 0278-0046, DOI: 10.1109/TIE.2005. 858734.

* cited by examiner

SYSTEM TO NOTIFY A REQUEST FOR HELP BY DETECTING AN INTENT TO PRESS A BUTTON, SAID SYSTEM USING ARTIFICIAL INTELLIGENCE

FIELD OF THE INVENTION

The invention relates to a system and a device for detecting an intent to operate an actuator, said system using artificial intelligence and triggering a function associated with the actuator.

BACKGROUND OF THE INVENTION

People generally associate actuators, like buttons and handles, with a means to trigger an operation. Examples of these operations are a call for help or the opening of a door, the starting/stopping of a machine, among many other operations.

Artificial intelligence (AI) is developing rapidly and AI applications are supporting or will support all industries including the aerospace industry, agriculture, chemical industry, computer industry, construction industry, defense industry, education industry, energy industry, entertainment industry, financial services industry, food industry, health care industry, hospitality industry, information industry, manufacturing, mass media, mining, telecommunication industry, transport industry, water industry and direct selling industry.

Computer vision or machine vision is an area of AI wherein machine learning can be used to classify or to categorize scenes in images of living beings and objects. Computer vision is also a science that tries to understand what can be seen and what is happening in an image or series of images such as a photo picture, a video or a live stream. To that extend, machine learning can be used. An image contains a scene reflecting people, animals and/or objects showing a pose and often executing an activity.

Human-machine communication have become more and more important. Machines that are able to process data, like computers, smartphones, tablets, cameras and robots, have deeply penetrated society.

WO2019193409, with title "System and method for user security and safety assistance", according to its abstract describes "A system and method for user security and safety assistance is provided. The system includes a service request receive module that enables system to receive at least one service request, associated with a physical security of said user or a person selected by said user, from said user through said user computing device, a service list display module that enables the system to receive a list of determined security services provided for the received service request from a central computing device and display said list on user interface of said system configured on said user computing device, a service selection module that enables the system to receive a selection of at least one security service selected from the list of determined security services, and a service request transmission module that enables the system to transmit the selected at least one security service to said central computing device via a network."

US20190306664, with title "Systems and methods for emergency communications", according to its abstract describes "Described herein are methods, devices, media, and systems for automatic public safety answering point lookup, location tracking of first responders, and facilitating data exchange during emergency communications."

U.S. Pat. No. 10,370,191, with title "Movable platform with a mechanical lift brake assembly", according to its abstract describes "Disclosed herein is a movable platform (MP) for moving freight during cross-dock operations. The MP comprises a mechanical lift brake assembly that can be utilized to deploy a plurality of mechanical lift brakes preventing further movement of the MP. AMP forklift attachment that can be used to convey the MP and to engage or disengage the mechanical lift brake assembly. The MP forklift attachment can be attached to a conveyance vehicle, such as a forklift, or built into an automated guided vehicle."

US20190300002, with title "System and method for responding to driver state", according to its abstract describes "A method for controlling vehicle systems includes receiving monitoring information from one or more monitoring systems and determining a plurality of driver states based on the monitoring information from the one or more monitoring systems. The method includes determining a combined driver state based on the plurality of driver states and modifying control of one or more vehicle systems based on the combined driver state"

US20190294871, with title "Human action data set generation in a machine learning system", according to its abstract describes "Methods, apparatuses, and computer-readable mediums for generating human action data sets are disclosed by the present disclosure. In an aspect, an apparatus may receive a set of reference images, where each of the images within the set of reference images includes a person, and a background image. The apparatus may identify body parts of the person from the set of reference image and generate a transformed skeleton image by mapping each of the body parts of the person to corresponding skeleton parts of a target skeleton. The apparatus may generate a mask of the transformed skeleton image. The apparatus may generate, using machine learning, a frame of the person formed according to the target skeleton within the background image."

U.S. Pat. No. 10,406,045, with title "Patient support apparatuses with navigation and guidance systems", according to its abstract describes "Patient support apparatuses, such as beds, cots, stretchers, recliners, or the like, include control systems with one or more image, radar, and/or laser sensors to detect objects and determine if a likelihood of collision exists. If so, the control system controls the speed and steering of the patient support apparatus in order to reduce the likelihood of collision. The control system may be adapted to autonomously drive the patient support apparatus, to transmit a message to a remote device indicating whether it is occupied by a patient or not, and/or to transmit its route to the remote device. The remote device may determine an estimate of a time of arrival of the patient support apparatus at a particular destination and/or determine a distance of the patient support apparatus from the particular destination."

SUMMARY OF THE INVENTION

The use of buttons and handles is a well-established technique to trigger or start execution of a function such a calling for help, opening a door, starting a machine, stopping a machine or any other process a person wants to trigger. People are used to the concept of buttons and handles.

Often it is preferable to attach many buttons and handles to various places (such as, but not limited to, walls, ceilings, vehicles, machines, furniture and street furniture) in order to provide the operation of one or more functions. These places are not always suitable for wiring these actuators or even connecting the actuators wirelessly. Even when connecting the actuators is possible, the costs for doing so can be high.

To that end, there is provided a system configured to trigger a function, said system comprising:
at least one actuator that is associated with said function;
an image capturing sensor;
a computing device comprising a data processor, and
a computer program product comprising a machine learning model trained for detecting an intent of a person to operate said at least one actuator,
wherein said computer program product when running on said data processor:
receives at least one image from said image capturing sensor;
analyzes said at least one image, the analyzing comprises:
subjecting said at least one image to said machine learning model;
detecting presence of said intent to operate said at least one actuator in said at least one image, and
triggers said function upon detecting said intent.

Nowadays computer vision allows computer systems to monitor people and their actions. For instance, it is possible to detect an action of a person with an intent to operate a button or a handle. Upon detection a function can be triggered without the need of actually pressing the button or pulling the handle. This is advantageous in various situation such as:
when a person is not able to reach a button or handle;
when it is favorable to have a backup for a possibly malfunctioning button or handle, and
when hygiene is better maintained when there is no direct contact with a person's body part.

Non-functional actuators don't have to be connected and can be much easier installed. In addition to costs reduction, non-functional actuators, such as dummy buttons (for instance stickers representing a button) and dummy handles are easier to be removed and easier to be relocated to a place where they are (more) needed, and therefore offer a more flexible solution.

In an embodiment of the system, the triggering of a function does not require a functional working actuator. Therefore, the system can be provided wherein said at least one actuator is a dummy.

In addition, in an embodiment the at least one actuator is selected from a button, a representation of a button, a picture of a button, a handle, a representation of a handle, a picture of a handle, and a combination thereof.

In an embodiment, the function is a request for help. In particular in these applications, it is possible to provide a series of actuators in an easy manner.

In an embodiment, the function comprises outputting a notification.

An image capturing sensor in an embodiment is a device that can provide an image or a series of images or a time series of images, in particular a digital image or digital picture. Such a device can comprise a camera of a filming (motion picture) device. Examples are devices comprising a CCD or similar imaging elements. Other examples are devices comprising a microphone for digitalizing sound into a sound image. Further examples of image capturing sensors are a camera, a sonar, a RADAR, a laser, LIDAR and an infrared camera. As such, these devices are known to a skilled person.

An image or a series of images or a time series of images result from said image capturing sensor or multiple devices of said image capturing sensor.

An intent to operate an actuator is in particular defined as a pose, an action or an activity of a living being to operate or start or begin to operate an actuator.

A living being is in particular defined as an animal or a human.

A subject can be living being, i.e. an animal or a person, or an object. A physical product is an example of an object, as is a car, a statue or a house.

A pose is the position and orientation of a subject. For humans and vertebrates with limbs, pose is defining the position of a body, limbs and head, in particular with respect to one another. The pose of living beings can be detected by articulated body pose estimation.

An action is in particular defined as a sequence of poses and may comprise a movement of a subject having trajectory.

An activity in an embodiment is a series of actions.

In general, a function relates, in particular transforms, input into output. A function in particular defined as one or more computer methods, or one or more operations of or on a system, or control of a system. A function is triggered, i.e., started or set in motion. In fact, in an embodiment triggering means to trigger the execution, to set in motion, or to start execution.

A computing device in an embodiment comprises one or more data processors. In an embodiment, it comprises a machine for automatically executing calculations or instructions. Examples (non-limiting) of computing device are a PC, a server, a cloud server, a locally distributed server environment, a computer cloud environment or any circuitry for performing particular functions in an electronic device.

A machine learning model trained for detecting an intent of a person to operate said at least one actuator may output a confidence value associated with one or more of the intent categories.

To that end, there is provided a method for categorizing an intent of a living being in a scene, comprising:
a computing device receiving a plurality of data points corresponding to said scene; the computing device determining at least one subsets of data points from said plurality of data points, wherein said at least one subsets of data points comprises said living being, said computing device categorizing said intent in said sub-scene, said computing device triggers a function based on said intent.

In some embodiments, once the computing device determines a categorization for the one or more subsets of data points, the computing device may store a given label associated with the determined category for the plurality of data points. The plurality of data points may then become part of the training data which may be used for future determinations of intents to operate at least one actuator.

A computing device may identify patterns using the machine learning algorithm to optimize in general the detection of an intent to operate an actuator and possibly in addition scene and context detection. For instance, the machine learning algorithm may indicate that scenes with a certain type of actuator comprise common characteristics, these characteristics may be a possible feature vector and utilized by the computing device (e.g. by the machine learning algorithm) to identify for instance a scene wherein a person is intending to operate a brake handle.

There is provided an AI system comprising a computing device running the computer program product.

There is further provided an apparatus comprising the AI system, wherein said scene comprises a representation of a surrounding of said apparatus comprising said intent of a person to operate at least one actuators, said AI system providing instructions to adjust at least one physical parameter of said apparatus based upon said categorizing of said intent of a person to operate at least one actuator. Such a physical parameter comprises at least one selected from speed, direction, pose, position, and orientation in a space.

In an embodiment, such an apparatus comprises an image capturing sensor described above. When furthermore provided with a local energy source, like a battery, and a wireless data transmission device, like a Bluetooth or WIFI device, an easy-installable system can be provided.

There is further provided a monitoring system comprising the AI system, wherein said scene comprises a representation of a surrounding of said monitoring system comprising said intent of a person to operate at least one actuator, said AI system providing a trigger based upon detection of said intent.

In an embodiment, triggering a function results in at least one of a notification, a control signal, a text message, an electromagnetic signal, an optical signal, a signal perceptible by senses of a living being or of a human being, a machine detectable or processable signal.

In an embodiment, the machine learning model is trained for detecting said intent using a series of images. In particular, the series of images comprises a time series forming part of a film. In an embodiment said computer program product when running on said data processor:
receives said series of images from said image capturing sensor;
analyzes said series of images, the analyzing comprises:
subjecting said series of images to said machine learning model;
detecting presence of said intent to operate said at least one actuator in said series of images.

In an embodiment, there is provided a surveillance system comprising the monitoring system described above.

A scene can be defined as a view of a place of an occurrence or action comprising at least one subject.

In an embodiment, the scene is an indoor scene.

In an embodiment, the scene is an outdoor scene.

In an embodiment, the scene comprises a series of subsequent poses defining said action. In an embodiment, a scene is recorded in part of a video.

In order to detect and localize a subject in a scene from a captured image, in an embodiment use is made of a method to detect subjects. Such a method will use machine learning techniques (mainly deep learning) to design and train a model which detects subjects given an input of a visual representation, e.g. an RGB image, as the system perceives. The model is trained on a large amount of annotated data; it comprises images with and without subjects and locations of the subjects are annotated.

In the case of deep learning, a detection framework such as Faster-RCNN, SSD, R-FCN, Mask-RCNN, or one of their derivatives can be used. A base model structure can be VGG, AlexNet, ResNet, GoogLeNet, adapted from the previous, or a new one. A model can be initialized with weights and trained similar tasks to improve and speedup the training Optimizing the weights of a model, in case of deep learning, can be done with the help of deep learning frameworks such as Tensorflow, Caffe, or MXNET. To train a model, optimization methods such as Adam or RMSProb can be used. Classification loss functions such Hinge Loss or Softmax Loss can be used. Other approaches which utilize handcrafted features (such as LBP, SIFT, or HOG) and conventional classification methods (such as SVM or Random Forest) can be used.

In order to detect and localize a living being in a scene from a retrieved image an embodiment uses a method to detect living beings. Such a method will use machine learning techniques (mainly deep learning) to design and train a model which detects living beings given an input of a visual representation, e.g. an RGB image, as the system perceives. The model is trained on a large amount of annotated data; it comprises images with and without living beings and locations of the living beings are annotated.

To detect bodily features, the system in an embodiment can determine key points on the body (e.g. hands, legs, shoulders, knees, etc.) of a living being.

To detect the key points on the body of a living being, in an embodiment the system comprises a model that is designed and trained for this detection. The training data to train the model comprises an annotation of various key points locations. When a new image is presented, the model allows identification of the locations of such key points. To this end, the system can utilize existing key point detection approaches such as MaskRCNN or CMU Part Affinity Fields.

The training procedure and data can be customized to best match the context of the content of the retrieved images. Such context may comprise an indoor context (e.g. a living room, bathroom, bedroom, kitchen, or a room within a care center, a hospital, a shop, a restaurant an office, a station, an airport, a theatre, a cinema, or in a train, a bus, airplane etc.) or an outdoor context (like a beach, a field, a street, a square, a park etc.) wherein there are changing lighting conditions.

For example, a pretrained deep neural network (DNN) on ImageNet, e.g. VGGNet, AlexNet, ResNet, Inception and Xception, can be adapted by taking the convolution layers from these pretrained DNN networks, and on top of them adding new layers specially designed for recognition of an intent to operate an actuator, and train the network as described for the model. Additional new layers could comprise specially designed layers for scene recognition, and pose and action recognition. All the aforementioned layers (recognition for an intent to operate an actuator, scene recognition, pose and action recognition) can be trained independently (along with/without the pre-trained conventional layers) or trained jointly in a multi-task fashion.

In an embodiment thereof or of the previous method, multiple images providing a time series are input in said machine learning model, and wherein said outputs of said machine learning model are concatenated as input for a further deep neural network to predict probabilities of each intent of a person to operate at least one actuator, present in the multiple images.

In this way, intentions of one or more persons to operate at least one actuator can be determined even better using time laps.

The multiple images can be processed sequentially. In an embodiment, the multiple images are processed parallel or semi-parallel. This allows near-real time of even real time processing.

Categorization may involve identifying to which of a set of categories (e.g. clear intent, fake intent, accidental intent, abnormal intent to operate a actuator) a new captured scene may belong, on the basis of a set of training data with known categories, such as the aforementioned categories. Categorization of the one or more subsets of data points associated with a captured scene may be performed using one or more machine learning algorithms and statistical classification algorithms Example algorithms may include linear classifiers (e.g. Fisher's linear discriminant, logistic regression, naive Bayes, and perceptron), support vector machines (e.g.

least squares support vector machines), clustering algorithms (e.g. k-means clustering), quadratic classifiers, multiclass classifiers, kernel estimation (e.g. k-nearest neighbor), boosting, decision trees (e.g. random forests), neural networks, Gene Expression Programming, Bayesian networks, hidden Markov models, binary classifiers, and learning vector quantization. Other example classification algorithms are also possible.

The process of categorization may involve the computing device determining, based on the output of the comparison of the one or more subsets with the one or more predetermined sets of scene types, a probability distribution (e.g. a Gaussian distribution) of possible scene types associated with the one or more subsets. Those skilled in the art will be aware that such a probability distribution may take the form of a discrete probability distribution, continuous probability distribution, and/or mixed continuous-discrete distributions. Other types of probability distributions are possible as well.

The term "statistically" when used herein, relates to dealing with the collection, analysis, interpretation, presentation, and organization of data. The analysis may be presented into visual formats like graphs, or other known graphical representations and/or tables.

The term "near real-time" or "nearly real-time" (NRT), in telecommunications and computing, refers to the time delay introduced, by automated data processing or network transmission, between the occurrence of an event and the use of the processed data, such as for display or feedback and control purposes. For example, a near-real-time display depicts an event or situation as it existed at the current time minus the processing time, as nearly the time of the live event.

The distinction between the terms "near real time" and "real time" is somewhat nebulous and must be defined for the situation at hand. The term implies that there are no significant delays. In many cases, processing described as "real-time" would be more accurately described as "near real-time". In fact, this may also be described as "functionally real-time". In particular, "functionally real-time" for a human being is experienced as being instantaneously. For instance, a button is pressed, and for a person pressing that button, a subsequent action is perceived as following directly upon pressing that button.

Near real-time also refers to delayed real-time transmission of voice and video. It allows playing video images, in approximately real-time, without having to wait for an entire large video file to download. Incompatible databases can export/import to common flat files that the other database can import/export on a scheduled basis so that they can sync/share common data in "near real-time" with each other.

Real-time signal processing is necessary, but not sufficient in and of itself, for live signal processing such as what is required in live event support. Live audio digital signal processing requires both real-time operation and a sufficient limit to throughput delay so as to be tolerable to performers using stage monitors or in-ear monitors and not noticeable as lip sync error by the audience also directly watching the performers. Tolerable limits to latency for live, real-time processing is a subject of investigation and debate but is estimated to be between 6 and 20 milliseconds.

A real-time system has been described in Wikipedia as one which "controls an environment by receiving data, processing them, and returning the results sufficiently quickly to affect the environment at that time". The term "real-time" is also used in simulation to mean that the simulation's clock runs at the same speed as a real clock, and in process control and enterprise systems to mean "without significant delay".

The distinction between "near real-time" and "real-time" varies, and the delay is dependent on the type and speed of the transmission. The delay in near real-time is typically of the order of several seconds to several minutes.

Often, systems that are described or seen as "real-time" are functionally real-time.

Demography in general is the statistical study of populations, especially human beings (see Wikipedia). As a very general science, it relates to analyzing any kind of dynamic living population, i.e., one that changes over time or space. Demography encompasses the study of the size, structure, and distribution of these populations, and spatial or temporal changes in them in response to birth, migration, aging, and death.

Demographic analysis can cover whole societies or groups defined by criteria such as education, nationality, religion, and ethnicity.

Formal demography limits its object of study to the measurement of population processes, while the broader field of social demography or population studies also analyses the relationships between economic, social, cultural, and biological processes influencing a population.

The common variables that are gathered in demographic research include age, sex, income level, race, employment, marital state, occupation, religion, location, home ownership and level of education. Demographics make certain generalizations about groups to identify customers. Additional demographic factors include gathering data on preferences, hobbies, lifestyle and more.

A camera is defined in for instance Wikipedia as an optical instrument for recording or capturing images, which may be stored locally, transmitted to another location, or both. The images may be individual still photographs or sequences of images constituting videos or movies. The camera is a remote sensing device as it senses subjects without any contact. Current cameras are in general digital image recording devices. A camera in general works with the light of the visible spectrum or with other portions of the electromagnetic spectrum. A still camera is an optical device which creates a single image of an object or scene and records it on an electronic sensor. A movie camera or a video camera operates similarly to a still camera, except it records a series of static images in rapid succession, commonly at a rate of 24 frames per second.

The term "substantially" herein, such as in "substantially all emission" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of".

The term "functionally" will be understood by, and be clear to, a person skilled in the art. The term "substantially" as well as "functionally" may also include embodiments with "entirely", "completely", "all", etc. Hence, in embodiments the adjective functionally may also be removed. When used, for instance in "functionally parallel", a skilled person will understand that the adjective "functionally" includes the term substantially as explained above. Functionally in particular is to be understood to include a configuration of features that allows these features to function as if the adjective "functionally" was not present. The term "functionally" is intended to cover variations in the feature to which it refers, and which variations are such that in the functional use of the feature, possibly in combination with other features it relates to in the invention, that combination of features is able to operate or function. For instance, if an antenna is functionally coupled or functionally connected to a communication device, received electromagnetic signals that are receives by the antenna can be used by the communication device. The word "functionally" as for instance used in "functionally parallel" is used to cover exactly parallel, but also the embodiments that are covered by the word "substantially" explained above. For instance, "functionally parallel" relates to embodiments that in operation function as if the parts are for instance parallel. This covers embodiments for which it is clear to a skilled person that it operates within its intended field of use as if it were parallel.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices or apparatus herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device or apparatus claims enumerating several means, several of these means may be embodied by one and the same item of hardware. The mere fact that certain measures are recited in mutually different dependent claims does not indicate that a combination of these measures cannot be used to advantage.

The invention further applies to an apparatus or device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Furthermore, some of the features can form the basis for one or more divisional applications.

BRIEF DESCRIPTION OF THE DRAWINGS

Embodiments of the invention will now be described, by way of example only, with reference to the accompanying schematic drawings in which corresponding reference symbols indicate corresponding parts, and in which.

The drawings are not necessarily on scale.

DESCRIPTION OF PREFERRED EMBODIMENTS

The following detailed description describes various features and functions of the disclosed systems and methods with reference to the accompanying figures. In the figures, similar symbols identify similar components, unless context dictates otherwise.

Figure 1A:
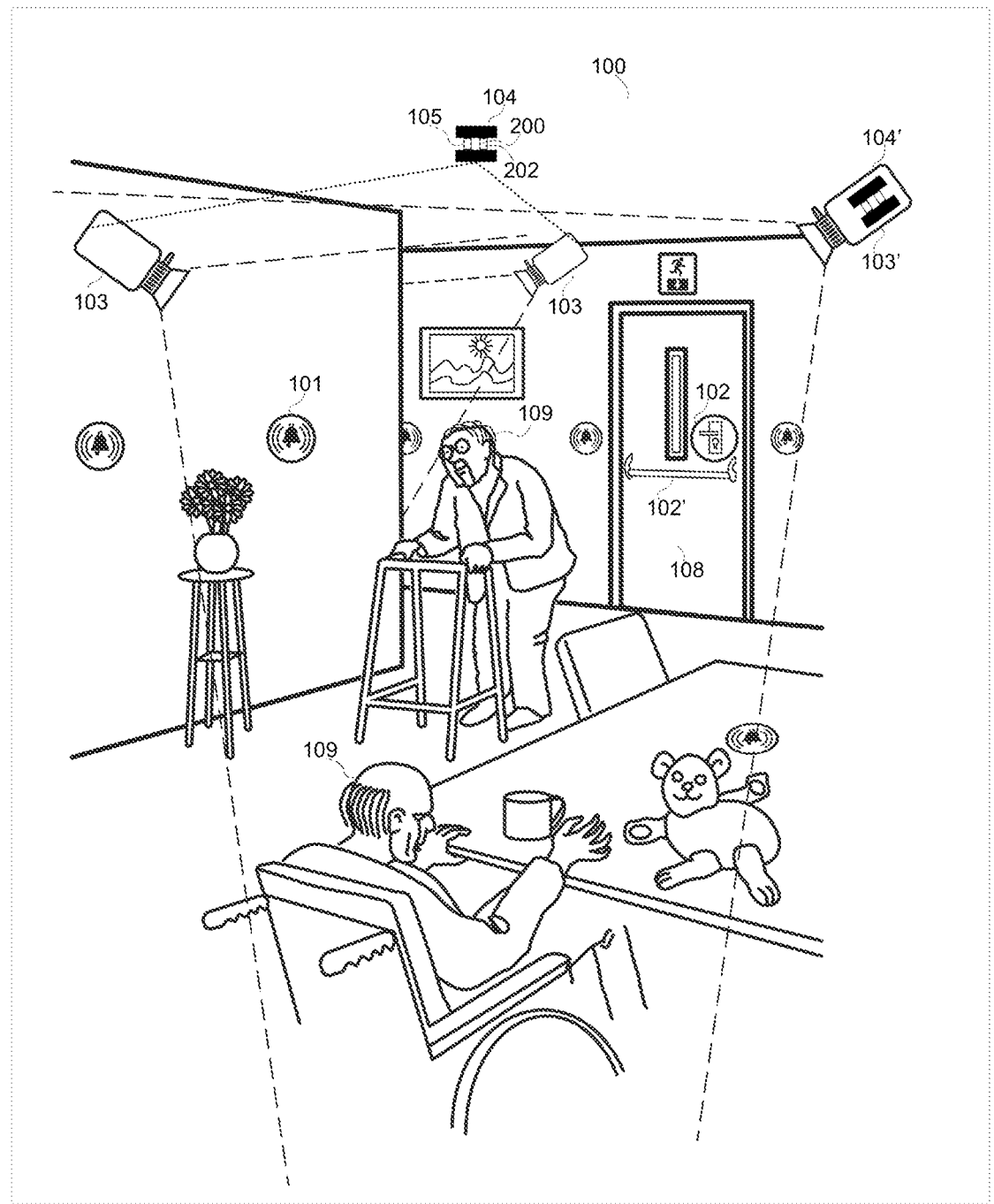
FIGS. 1A-1E depicts sample embodiments of systems configured to trigger a function.

FIG. 1A depicts an example 100 of an embodiment showing an elderly home that has been provided with many buttons 101, located on the wall and table, that allow people to call for help by just an intent of pressing a button. Similar there are handles, 102 and 102', attached to a door 108 that allow people to open the door 108 by just an intent to push them. Image capturing devices 103 and 103' are cameras monitoring the actuators (101, 102 and 102'). In fact, these cameras may also monitor a broader field of view.

A computer program product 200 (FIG. 2) comprising a machine learning model 202 (FIG. 2), running on a data processor 105 of a computing device 104, receives at least one image from the image capturing devices 103.

When the at least one image comprises an intent of a person 109 to press a button 101, a help function is triggered or starts to be executed by the computer program product 200.

When the at least one image comprises an intent of a person 109 to push a handle, 102 or 102', a function to open the door 108 is triggered by the computer program product 200.

Image capturing device 103' is a camera with a built-in computing device 104' comprising a data processor and a computer program product 200 comprising a machine learning model 202. The computer program product when running on the data processor receives at least one image from camera 103'. The computer program product then can analyze the at least one image by subjecting the at least one image to the machine learning model 202 for detecting an intent of a person 109 to press a button 101, and upon detecting the intent the computer program product 200 triggers a help function. The computer program product then also or instead can analyze the at least one image by subjecting the at least one image to the machine learning model 202 for detecting an intent of a person 109 to push a handle, 102 or 102', and upon detecting the intent the computer program product 200 triggers a function to open the door 108. In an embodiment, the camera 103, 103' comprises a local power source, like a battery, and a wireless data transmission device for coupling to a remote computer device. In this way, installing the system is even easier.

Figure 1B:
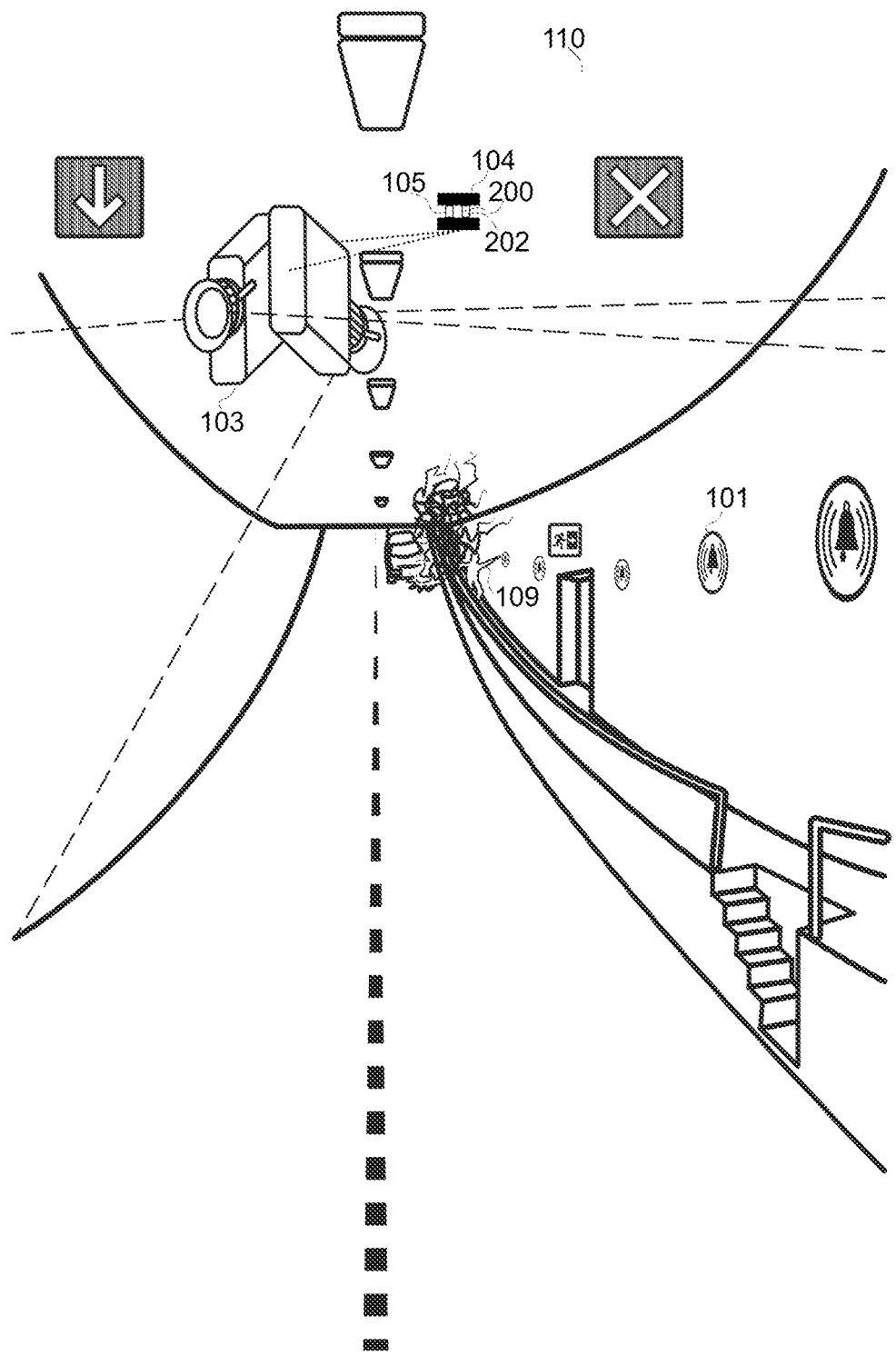

FIG. 1B depicts an example 110 of an embodiment, showing a tunnel, for vehicles, provided with many alarm buttons 101, located on the wall, that allow persons in danger to trigger an alarm by just an intent of pressing a button 101. Image capturing devices 103 monitor the buttons 101.

Similar to FIG. 1A, image capturing devices 103 are cameras monitoring the buttons 101. A computer program product 200 comprising a machine learning model 202, running on a data processor 105 of a computing device 104, receives at least one image from the image capturing devices 103.

When the at least one image comprises an intent of a person 109 to press a button 101, an alarm function is triggered by said computer program product 200.

Figure 1C:
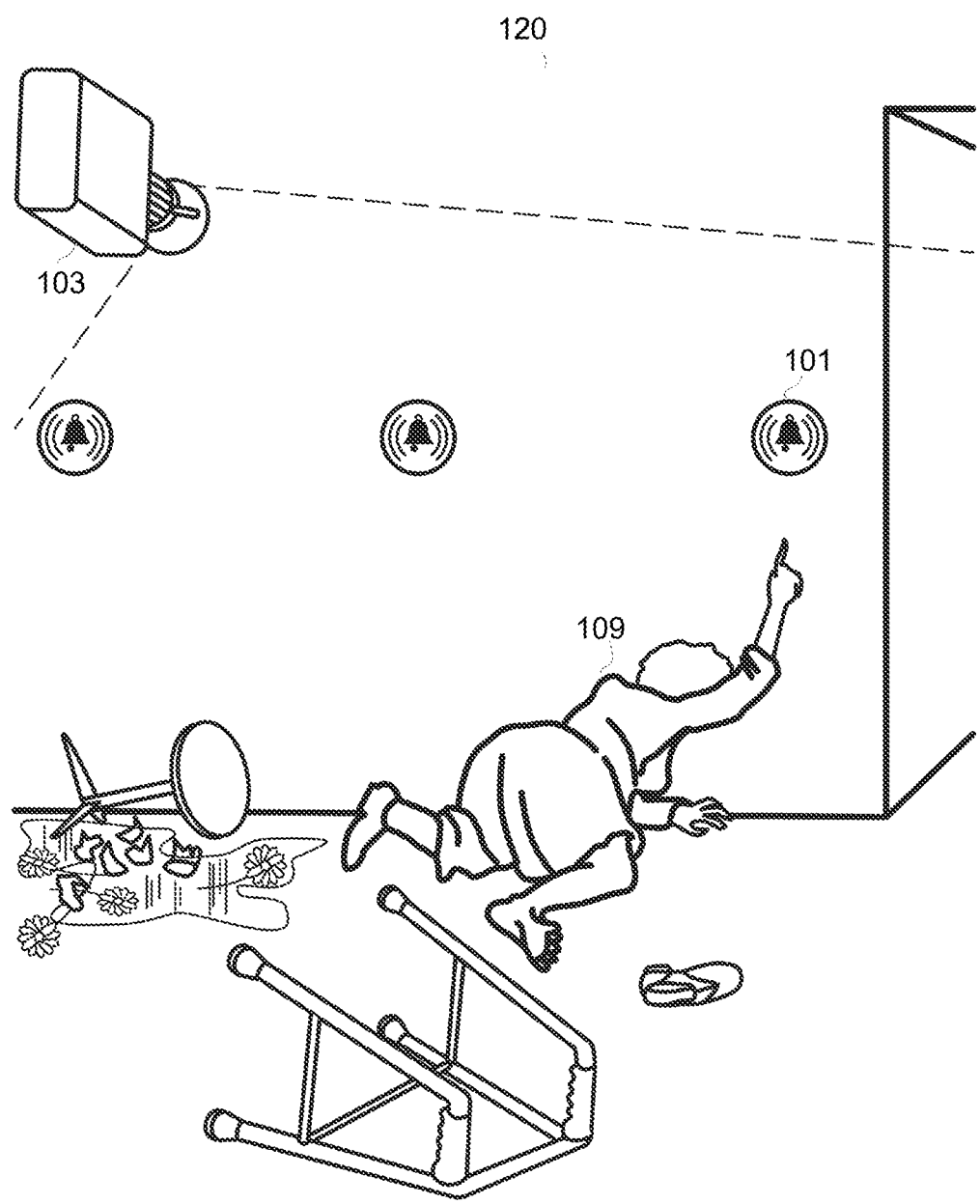

FIG. 1C depicts a further example 120 of an embodiment. In this example, an elderly person 109 fell down. The elderly person 109 tries to press a button 101 on a wall which is monitored by a camera 103. In this exemplary embodiment, an intent by the elderly person 109 to press a button 101 is detected and that intent is recorded and processed, and the computer program product then triggers an alarm so the elderly person 109 can be assisted.

Figure 1D:
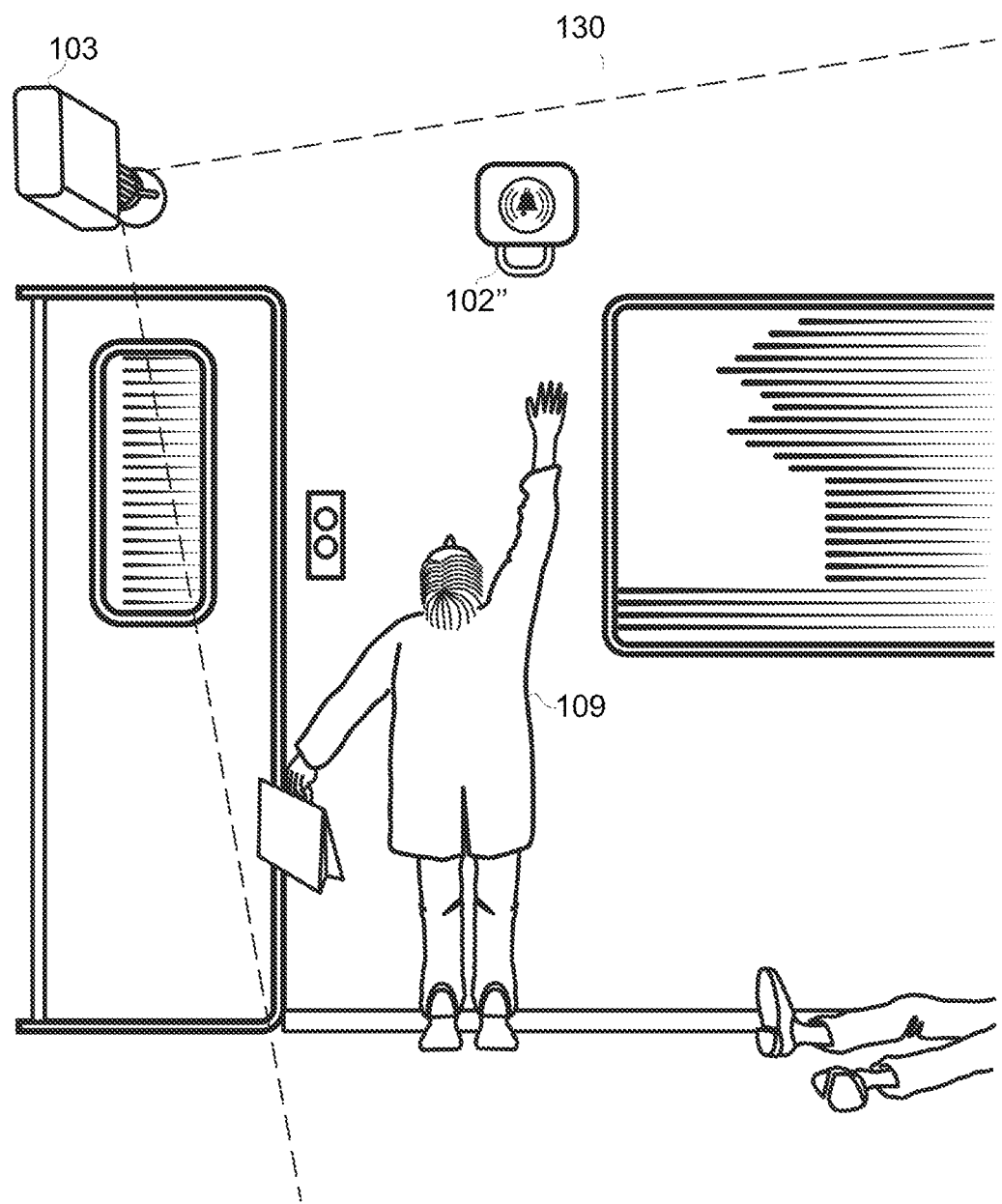

FIG. 1D depicts an example 130 of an embodiment showing a person 109 who tries to reach for an emergency break handle 102" of a train which is monitored by a camera 103. In this embodiment, an intent by the person 109 to pull the emergency break handle 102" is detected and triggers the train to start an emergency procedure, for instance stop the train via an emergency brake procedure. In fact, as the process is automated, it allows the system before actually braking, check some other conditions.

Figure 1E:
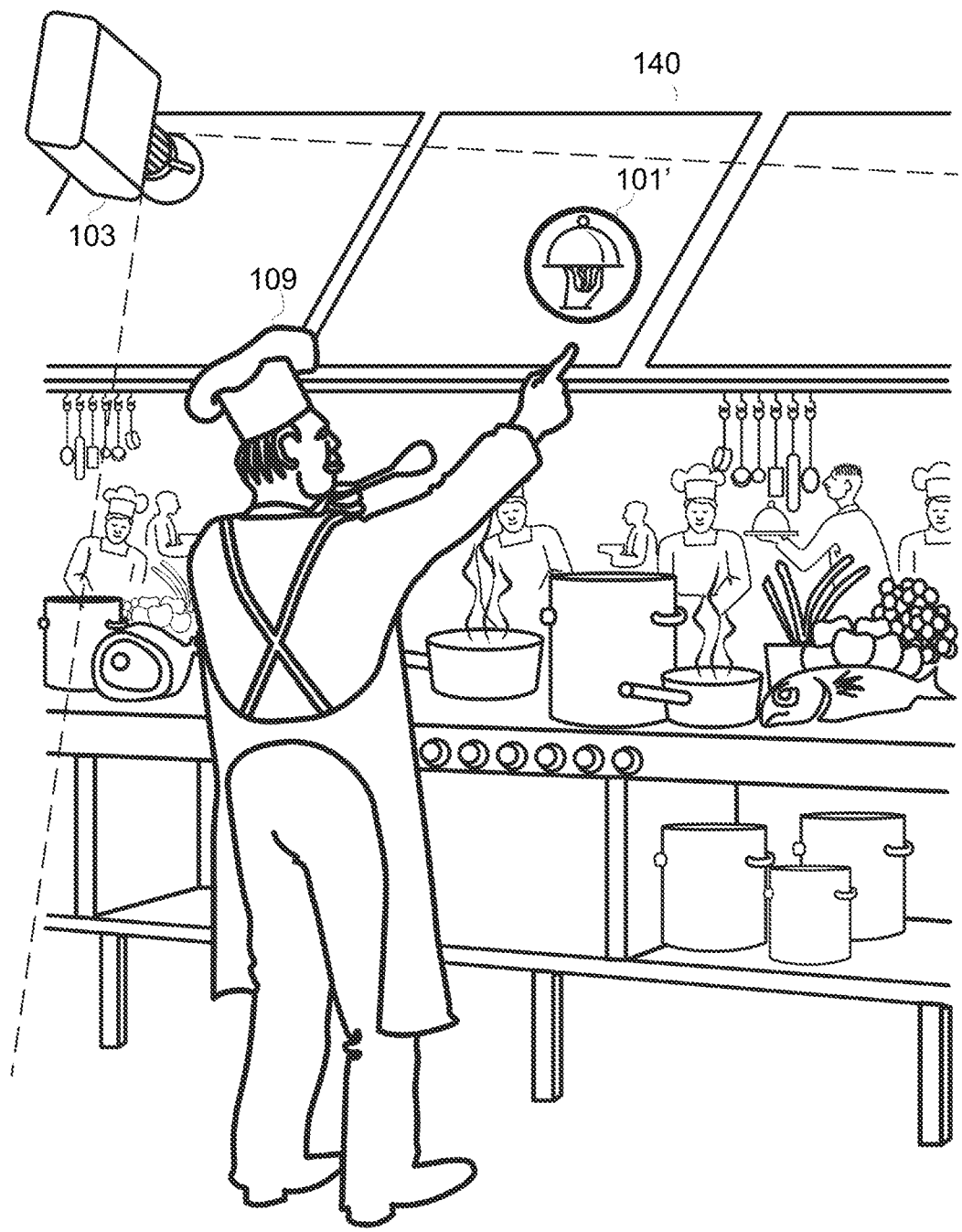

FIG. 1E depicts an example 140 of an embodiment, showing a chef 109 with greasy fingers pointing to a button 101' which is monitored by a camera 103. In this embodiment, the mere pointing of chef 109 to button 101' is detected and triggers a notification to waiting staff that a dish is ready. The chef 109 does not need to touch the button 101.

In other examples, for instance in public places, bathrooms and hospitals, hygiene will also benefit when direct contact with actuators is avoided.

In another embodiment of the current invention, the actuator can be part of an industrial process to be operated by a person.

In a further embodiment of the current invention, the actuator can be part of a vehicle to be operated by a person.

Figure 2:
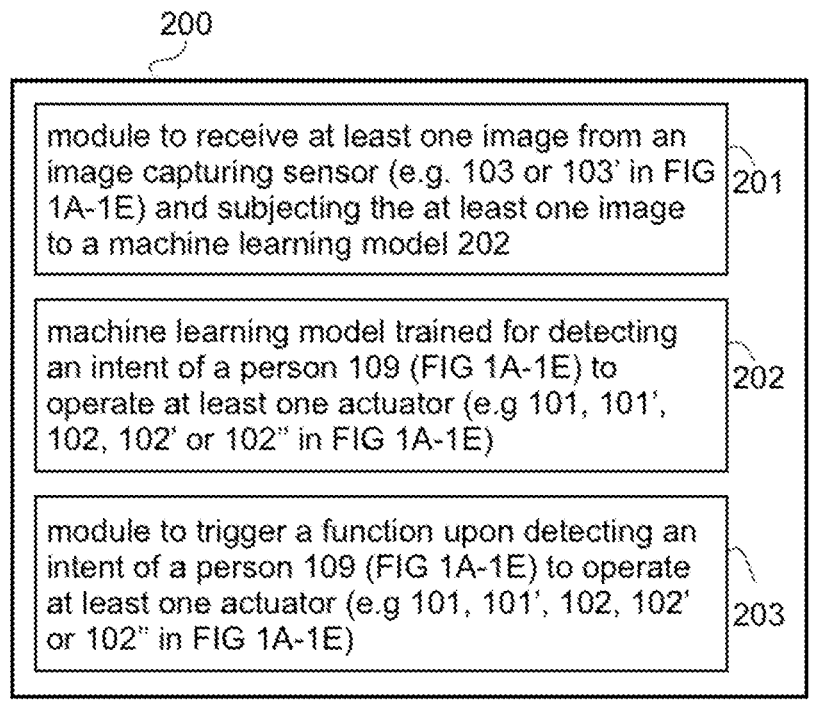
FIG. 2 depicts a simplified block diagram of a computer program product configured to trigger a function upon an intent of a person to operate an actuator.

FIG. 2 depicts a simplified block diagram of a computer program product 200 configured to trigger a function upon detecting an intent of a person to operate at least one actuator, in accordance with an example embodiment. Components coupled to or included in the computer program product 200 may include a component 201, i.e. a module to receive at least one image from an image capturing sensor (e.g. 103 or 103' in FIGS. 1A-1E) and subjecting the at least one image to a machine learning model 202, and may include a component 202, i.e. a machine learning model trained for detecting an intent of a person 109 (FIGS. 1A-1E) to operate at least one actuator (e.g. 101, 101', 102, 102' or 102" in FIGS. 1A-1E), and may include a component 203, i.e. a module to trigger a function upon detecting an intent of a person 109 (FIGS. 1A-1E) to operate at least one actuator (e.g. 101, 101', 102, 102' or 102" in FIGS. 1A-1E).

In other embodiments, the computer program product 200 may include more, fewer, or different systems, and each system may include more, fewer, or different components. Additionally, the systems and components shown may be combined or divided in any number of ways.

In an embodiment a component 202 takes as input the at least one image comprising a plurality of data points and labels a subset of the plurality of data points that corresponds to at least one intent of a person 109 (FIGS. 1A-1E) to operate at least one actuator (e.g. 101, 101', 102, 102' or 102" in FIGS. 1A-1E).

In a further embodiment a component 202 receives an input comprising the at least one image comprising a plurality of data points and labels multiple subsets of the plurality of data points that corresponds to at least one intent of a person 109 (FIGS. 1A-1E) to operate at least one actuator (e.g. 101, 101', 102, 102' or 102" in FIGS. 1A-1E).

In an embodiment related to animal, a machine learning model is trained for detecting an intent of an animal to operate at least one actuator (e.g. 101, 101', 102, 102' or 102" in FIGS. 1A-1E).

Figure 3:
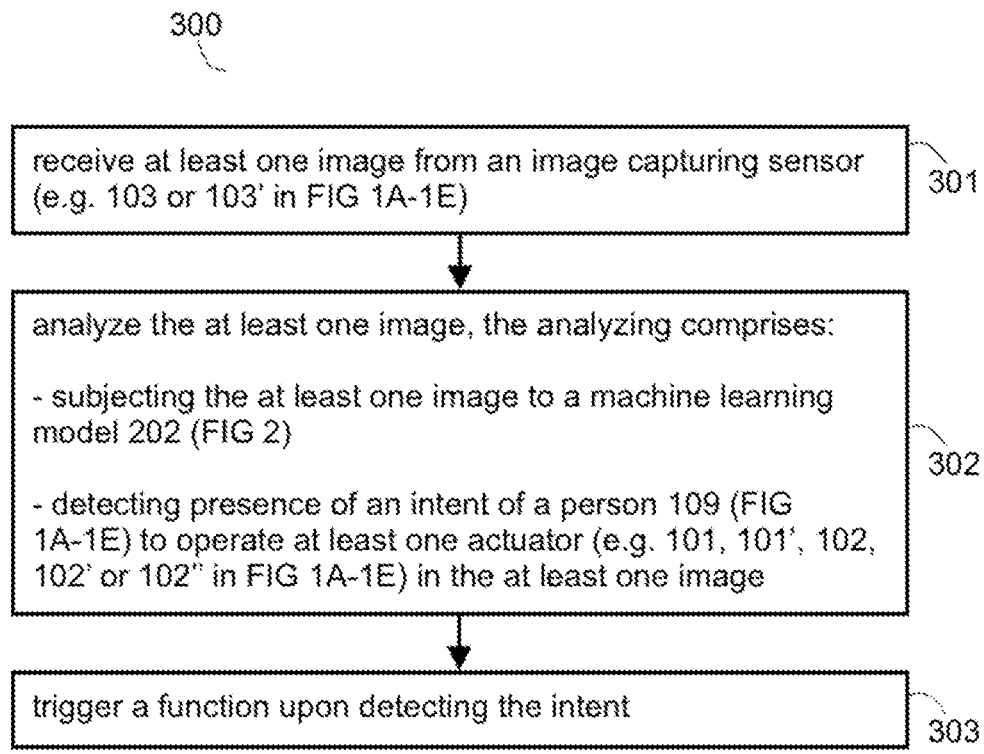
FIG. 3 depicts a flow chart of an example method for triggering a function upon an intent of a person to operate an actuator.

FIG. 3 depicts a flow chart of an example method 300 to trigger a function upon detecting an intent of a person 109 (FIGS. 1A-1E) to operate at least one actuator (e.g. 101, 101', 102, 102' or 102" in FIGS. 1A-1E). The method 300 may include one or more operations, functions, or actions as illustrated by one or more of blocks 301-303. Although the blocks are illustrated in a sequential order, these blocks may in some instances be performed in parallel. Also, the various blocks may be combined into fewer blocks, divided into additional blocks, and/or removed based upon the desired implementation.

In addition, for the method 300 and other processes and methods disclosed herein, the flow chart shows functionality and operation of one possible implementation of present embodiments. In this regard, each block may represent a module, a segment, or a portion of program code, which includes one or more instructions executable by a data processor for implementing specific logical functions or steps in the process. The computer program product 200 (FIG. 2) may be stored on any type of computer readable medium or memory, for example a storage device including a disk or hard drive.

In addition, for the method 300 and other processes and methods disclosed herein, each block in FIG. 3 may represent circuitry that is wired to perform the specific logical functions in the process. For the sake of example, the method 300 shown in FIG. 3 will be described as implemented by an example computer program product such as the computer program product 200 (FIG. 2). The method 300 can also be described as implemented by a camera or computing device, as the computing device and the computer program product may be onboard the camera or may be off-board but in wired or wireless communication with the camera. Therefore, the terms "computer device", "computer program product" and "camera" can be interchangeable herein. It should be understood that other entities or combinations of entities can implement one or more steps of the example method 300.

At block 301, the method 300 includes: receive at least one image from an image capturing sensor (e.g. 103 or 103' in FIGS. 1A-1E).

In an embodiment the at least one image (e.g. a plurality of data points) corresponds to the view of a camera.

In a further embodiment, the at least one image corresponds to LIDAR/RADAR-based information that may be indicative, for example, of dimensional parameters of a given subject, and may indicate whether the given subject is stationary or moving.

At block 302, the method 300 includes: analyze the at least one image, the analyzing comprises:
- subjecting the at least one image to a machine learning model 202 (FIG. 2);
- detecting presence of an intent of a person 109 (FIGS. 1A-1E) to operate at least one actuator (e.g. 101, 101', 102, 102' or 102" in FIGS. 1A-1E) in the at least one image.

At block 303, the method 300 includes: trigger a function upon detecting the intent.

Although listed in a sequential order, these actions for the analyzing may in some instances be performed in parallel. Also, the various actions may be combined into fewer actions, divided into additional actions, and/or removed based upon the desired implementation.

In this context the computer readable medium may include a non-transitory computer readable medium, for example, such as computer-readable media that stores data for short periods of time like register memory, processor cache and Random Access Memory (RAM). The computer readable medium may also include non-transitory media or memory, such as secondary or persistent long term storage, like read only memory (ROM), optical or magnetic or solid state disks/drives, compact-disc read only memory (CD-ROM), for example. The computer readable media may also be any other volatile or non-volatile storage systems. The computer readable medium may be considered a computer readable storage medium, a tangible storage device, or other article of manufacture, for example.

The embodiments described earlier can be combined with any of the aforementioned methods described.

It will also be clear that the above description and drawings are included to illustrate some embodiments of the invention, and not to limit the scope of protection. Starting from this disclosure, many more embodiments will be evident to a skilled person. These embodiments are within the scope of protection and the essence of this invention and are obvious combinations of prior art techniques and the disclosure of this patent.

The invention claimed is:

1. A surveillance system configured to trigger a request for help from a person, said system comprising:
   at least one dummy actuator that is associated with said request for help;
   an image capturing sensor;
   a computing device comprising a data processor, and
   a computer program product comprising a machine learning model trained for detecting an intent of said person to operate said at least one dummy actuator,
   wherein said computer program product when running on said data processor:
      receives at least one image from said image capturing sensor;
      analyzes said at least one image, the analyzing comprises:
         subjecting said at least one image to said machine learning model;
         detecting presence of said intent to operate said at least one dummy actuator in said at least one image, and
         outputs a notification upon detecting said intent.

2. The system according to claim 1, wherein said at least one dummy actuator is selected from a button, a representation of a button, a picture of a button, a handle, a representation of a handle, a picture of a handle, and a combination thereof.

3. The system according to claim 1, wherein said machine learning model is trained for detecting said intent using a series of images, wherein said computer program product when running on said data processor:
   receives said series of images from said image capturing sensor;
   analyzes said series of images, the analyzing comprises:
      subjecting said series of images to said machine learning model;
      detecting presence of said intent to operate said at least one actuator in said series of images.

4. The system according to claim 1, wherein data processor is configured to analyze said received image or series of images substantially real-time.

* * * * *